United States Patent
Asrar et al.

(10) Patent No.: US 6,204,341 B1
(45) Date of Patent: Mar. 20, 2001

(54) HYDROXY-TERMINATED POLYHYDROXYALKANOATES

(75) Inventors: Jawed Asrar; Devang T. Shah, both of Chesterfield; Minhtien Tran, Ballwin, all of MO (US)

(73) Assignee: Monsanto Company, St Louis, MO (US)

(*) Notice: Subject to any disclaimer, the term of this patent is extended or adjusted under 35 U.S.C. 154(b) by 0 days.

(21) Appl. No.: 09/410,708

(22) Filed: Oct. 1, 1999

Related U.S. Application Data

(62) Division of application No. 09/063,256, filed on Apr. 20, 1998, now Pat. No. 5,994,478.
(60) Provisional application No. 60/044,042, filed on Apr. 21, 1997.

(51) Int. Cl.⁷ ...................................................... C08F 20/00
(52) U.S. Cl. .......................... 525/437; 525/444; 525/450
(58) Field of Search .................................... 525/450, 437, 525/444

(56) References Cited

U.S. PATENT DOCUMENTS

| | | | |
|---|---|---|---|
| 5,120,802 | | 6/1992 | Mares et al. |
| 5,225,227 | * | 7/1993 | Yalpani ................................ 426/580 |
| 5,229,158 | * | 7/1993 | Yalpani ................................ 426/565 |
| 5,395,919 | * | 3/1995 | Lee et al. ............................. 528/361 |
| 5,434,062 | * | 7/1995 | Groleau et al. ...................... 435/135 |
| 5,550,173 | * | 8/1996 | Hammond et al. .................. 523/122 |
| 5,625,030 | | 4/1997 | Williams et al. |
| 5,693,389 | * | 12/1997 | Liggat .................................. 428/35.7 |
| 5,753,782 | * | 5/1998 | Hammond et al. .................. 525/450 |
| 5,811,272 | * | 9/1998 | Snell et al. ........................... 435/135 |
| 5,939,467 | * | 8/1999 | Wnuk et al. ......................... 523/128 |

FOREIGN PATENT DOCUMENTS

| | | |
|---|---|---|
| 19 66 923 | 5/1975 | (DE) . |
| 0 304 293 | 2/1989 | (EP) . |
| 0 440 165 | 8/1991 | (EP) . |
| 2 272 904 | 6/1994 | (GB) . |
| 94/12652 | 6/1994 | (WO) . |

OTHER PUBLICATIONS

Hirt, Thomas D. et al. (1996) "Telechelic diols from poly [(R)–3–hydroxybutyric acid] and poly {[(R)–3–hydroxybutyric acid]–co–[(R)–3–hydroxyvaleric acid]}," *Macromol. Chem. Phys.* 197:1609–1614.

Shi, Fengying et al. (1996) "Use of Poly(ethylene glycol)s To Regulate Poly(3–hydroxybutyrate) Molecular Weight dueing *Alcaligenes eutrophus* Cultivations," *Macromolecules* 29:7753–7758.

* cited by examiner

*Primary Examiner*—Nathan M. Nutter
(74) *Attorney, Agent, or Firm*—Jon Beusen; Howrey Simon Arnold & White

(57) ABSTRACT

Hydroxyterminated PHA is produced by cultivating a PHA-producing microorganism in the presence of an aliphatic diol or an aliphatic polyol. High molecular weight hydroxy-terminated PHA is obtainable by the disclosed process, and is useful in the production of graft, block and random polymers and copolymers with other monomers, oligomers and polymers containing appropriate functionality and end group compatibility.

6 Claims, 1 Drawing Sheet

HYDROXY-TERMINATED POLYHYDROXYALKANOATES

This is a divisional of application Ser. No. 09/063,256 filed Apr. 20, 1998 and now U.S. Pat. No. 5,994,478 which application claims priority of Provisional Application No. 60/044,042, filed Apr. 21, 1997.

BACKGROUND OF THE INVENTION

The present invention relates generally to biodegradable polymers. More particularly, it concerns methods for the bioproduction of novel hydroxy-terminated polyhydroxyalkanoate (PHA) polymer compositions, and their subsequent use in production of novel copolyesters, polyester carbonates, polyester ethers, polyester urethanes, polyester amides, polyester acetals and other elastomeric, thermoplastic and thermoset polymers and copolymers.

There has been considerable interest in recent years in the use of biodegradable polymers to address concerns over plastic waste accumulation. The potential worldwide market for biodegradable polymers is enormous (>10B lbs/yr). Some of the markets and applications most amenable to the use of such biopolymers range from single use applications, which include packaging, personal hygiene, garbage bags, and others where the biopolymers become soiled and are ideally suited for biodegradation through composting, to markets and applications in which the biopolymers can be recovered as clean materials, such as garment bags, shopping bags, grocery bags, etc. and are suitable for recycling, as well as composting, or biodegradation in landfills.

PHA biopolymers are thermoplastic polyesters produced by numerous microorganisms in response to nutrient limitation. The commercial potential for PHA's spans many industries, and is derived primarily from certain advantageous properties which distinguish PHA polymers from petrochemical-derived polymers, namely excellent biodegradability and natural renewability.

Widespread use and acceptance of PHA's, however, has been hindered by certain undesirable chemical and physical properties of these polymers. For example, PHA's are among the most thermosensitive of all commercially available polymers. As such, the rate of polymer degradation, as measured by a decrease in molecular weight, increases sharply with increasing temperatures in the range typically required for conventional melt-processing of PHA's into end-products such as films, coatings, fibers etc. An additional limitation of the potential utility of PHA polymers relates to the observation that some polymer characteristics, for example ductility, elongation, impact resistance, and flexibility, diminish over time. This rapid "aging" of certain PHA-derived products is unacceptable for many applications. Thus, the success of PHA as a viable alternative to both petrochemical-derived polymers and to non-PHA biodegradable polymers, will depend upon novel approaches to overcome the unique difficulties associated with PHA polymers and with products derived therefrom.

One approach which has the potential to provide new classes of PHA-containing polymers having unique and improved properties, is based on graft, random and block polymers and copolymers. In generating such polymers and copolymers, it is possible to vary the nature, length and mass fraction of the different polymer constituents which are present. In doing so, the morphology of the polymer, and therefore the resulting properties, may be manipulated to meet the requirements of a given application.

The production of copolymers with PHA is limited, however, by the dissimilar ends of a PHA polymer chain (i.e. a carboxy group and a hydroxy group, respectively, on the ends of each polymer molecule). In order for PHA to be useful in the production of copolymers, it is desired that the ends of a polymer molecule chain possess the same chemical groups, and that those groups be capable of forming covalent bonds with the ends of other polymer molecules either by direct reaction or by use of a coupling agent (e.g. a diisocyanate). The reactive end groups of hydroxy-terminated PHA, for example, would be well suited for the preparation of high MW block copolymers by various known chain extension approaches.

Synthetic PHA hydroxy-termination has been reported. Hirt et al. (Macromol. Chem. Phys. 197, 1609–1614 (1996)) describe a method for the preparation of HO-terminated PHB and PHB/HV by a transesterification procedure using ethylene glycol and commercial grade PHB and PHBV (Biopol) in the presence of a catalyst. When catalysts such as $H_3PO_4$, ethylene glycolate, or tripropyl amine were used, some diol was formed but the major products were oligomers with carboxylic acid end groups and olefinic end groups, even when a tenfold excess of ethylene glycol was used. When dibutyltin-dilaurate was used as catalyst with a 10-fold excess of ethylene glycol, end-group hydroxyl incorporation was obtained. The oligomer had a hydroxyl end-group content of ~97%, but the molecular weight (Mn) of the hydroxy-terminated PHA obtained by Hirt et. al. was only about 2,300. The ratio of the weight- to number-average molecular weights (Mw/Mn) of their oligomers was ~2.

When one prepares hydroxy-terminated PHA by reaction of PHA with EG in the presence of a catalyst, a steady decline in MW to less than about 3,000 is observed as the content of hydroxyl end groups increases from about 50% to greater than 80%. Experiments performed in our laboratory confirm this effect. (the results of which are presented in Example 1 and in FIG. 1).

For many applications, higher MW hydroxy-terminated PHA would be preferred for use in the preparation of copolymers. In addition, it would be advantageous to have the ability to produce hydroxy-terminated PHA by a simple and inexpensive method that is easily amenable to large scale polymer production.

Shi et al (Macromolecules 29 10–17 (1996)) reported in vivo formation of a hybrid natural-synthetic di-block copolymer. They describe a method to prepare PHA-polyethylene glycol (PEG) di-block copolymers where the carboxylate terminus of PHA chains are covalently linked by an ester bond to PEG chain segments. Polymer production was carried out by cultivation of *A. eutrophus* in a nitrogen free medium containing 4-HBA and 4% w/v PEG (Mn~200). The unfractionated product was complex in that it was composed of at least three different component polymers of different repeat unit composition. The product was separated into an acetone insoluble fraction (43% w/w, Mn~130 k, Mw/Mn~3.42) and an acetone soluble fraction (57% w/w, Mn~37.4 k, Mw/Mn~2.52). The mole fraction content of 3HB, 3HV, 4HB, and PEG in the acetone insoluble and acetone soluble fractions were 95, 2, 3, 0.1 and 13, 2, 84, 1.6, respectively. Thus the PEG segments were found primarily in the acetone soluble fraction. It is important to note that the acetone soluble fraction is high in 4HB while the acetone insoluble fraction is high in 3HB. This process to make the di-block copolymer is not very selective.

Shi. et. al. (Macromolecules 29 7753–8 (1996)) later reported the use of PEG's to regulate MW during A.

eutrophus cultivations. They used PEG's that ranged in MW from is PEG-106 (diethylene glycol) up to PEG-10,000 (MW~10 k) and reported that PEG-106 was the most effective in that only 0.25% was required to reduce Mn of the PHA by 74%. By adding 10% PEG-106 to the medium, the decrease in Mn was from 455 k to 19.4 k. They also reported that the use of monomethoxy ether CH3O-PEG-OH-350 and PEG-300 resulted in almost identical molecular weight reductions. However, the dimethoxy ether of tetraethylene glycol was not an effective agent for molecular weight reduction. Thus, the chain end functionality useful in the work was a hydroxyl group. Shi et al. also reported that their PHA products did not contain PEG terminal groups. They concluded that molecular weight reduction was not due to chain termination reactions by PEG, but likely due to interaction between PEG and the PHA production system, leading to an increased rate of chain termination by water relative to chain propagation reactions.

We have now discovered that by using simple, monomeric aliphatic diols or aliphatic polyols, that clean and selective reactions can be obtained by in vivo formation of PHA-diols at concentrations of aliphatic diols or aliphatic polyols in the culture medium that are not toxic to the PHA-producing microorganisms.

SUMMARY OF THE INVENTION

In accordance with a first aspect of the present invention, there is provided a method of making linear or branched hydroxy-terminated PHA in a PHA-producing microorganism by cultivating the microorganism in the presence of an aliphatic diol or an aliphatic polyol. Typically, the aliphatic diol or aliphatic polyol is present in the cultivating medium at a concentration between about 0.1 and 5% w/v. The PHA compositions obtainable by this method have desirably high MW and % HO-content.

Many of the aliphatic diols suitable for use in the present invention are represented by structures (1) and (2) below:

(1)

where n=0–25;

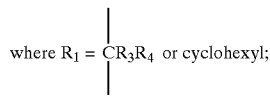

$R_2$=H or $CH_3(CH_2)_m$—, where m=0–25;
$R_3$ and $R_4$=H or $CH_3(CH_2)_p$— where p=0–25.

(2)

where n=1–10.

Examples of preferred aliphatic diols include ethylene glycol (EG), propylene glycol (PG), 1,3-propanediol (1,3-PD), neopentyl glycol (NG), 1,4-butanediol (1,4-BD), 1,4-cyclohexyldimethanol (1,4CHDM), 1,6-hexanediol (1,6-HD), diethylene glycol (DEG) and tetraethylene glycol (TEG) for linear hydroxy-terminated PHA's.

Many of the aliphatic polyols for use in the present invention are represented by structure (3) below:

(3)

where n=1–12;

$R_4$=H or $CH_3(CH_2)_m$— where m=0–25.

Examples of preferred aliphatic polyols include glycerol (GL), pentaerythritol (PAE), sorbitol (SL), mannitol (ML), etc. for branched or star-shaped hydroxy-terminated PHA's. Also dianhydro derivatives of the aliphatic polyols, such as 1,4:3,6-dianhydrosorbitol or 1,4:3,6-dianhydroglucitol, could be used.

The method according to the first aspect of the present invention can be used with any PHA-producing microorganism, either natural or recombinant. It is well known in the art that nunerous microorganisms are capable of PHA production. For example, strains from bacterial genus Alcaligenes (e.g. *eutrophus, latus*), Bacillus (e.g. *subtilis, megaterium*), Pseudomonas (e.g. *oleovorans, putida, fluorescent*), Aeromonas (e.g. *caviae, hydrophila*), *Azotobacter vinelandii, Comamonas testosteroni*, and others, produce PHA. *Alcaligenes eutrophus, Alcaligenes latus*, and *Comamonas testosteroni* are demonstrated herein as examples of PHA-producing microorganism suitable for use in the production of hydroxy-terminated PHA's. Based on the present disclosure, one skilled in the art would recognize and appreciate that the methods described herein can be performed using essentially any PHA-producing microorganism.

In accordance with a further aspect of the present invention, there are provided hydroxy-terminated PHA compositions produced by the methods of the first aspect of the present invention. The compositions have desirably high molecular weights, ranging up to greater than 100,000, suitable for use in the production of novel polymer and copolymer compositions with advantageous characteristics. In addition, the PHA compositions so produced have %HO-contents greater than 50%, preferably greater than 80%, and more preferably greater than 90%.

In accordance with a further aspect of this invention, there are provided methods of using said hydroxy-terminated PHA compositions in the preparation of graft, block or random polymers and copolymers, and the polymer and copolymer compositions produced therefrom. The polymer and copolymer compositions of the present invention comprise reaction products of hydroxy-terminated PHA and one or more additional suitable polymers, oligomers, or monomers having desired functionality. The hydroxy-terminated PHA is typically reacted with a suitable monomeric or oligomeric coupling agent, and may be further reacted with another hydroxy-terminated moiety. For example, a block copolymer can be produced which contains hydroxy-terminated PHA and a hydroxy-terminated aliphatic polyester or polyether, such as hydroxy-terminated polyoxyethylenes, polycaprolactone diol, polybutylene succinate diol, polyethylene succinate diol, polybutylene succinate cobutylene adipate diol, or other hydroxy-terminated polyether, polyester, or copolyester diols, linked with an appropriate coupling agent.

BRIEF DESCRIPTION OF THE DRAWING

The following drawing forms part of the present specification and is included to further demonstrate certain aspects of the present invention. The invention may be better understood by reference to this drawing in combination with the detailed description of specific embodiments presented herein.

DESCRIPTION OF ILLUSTRATIVE EMBODIMENTS

Figure 1:
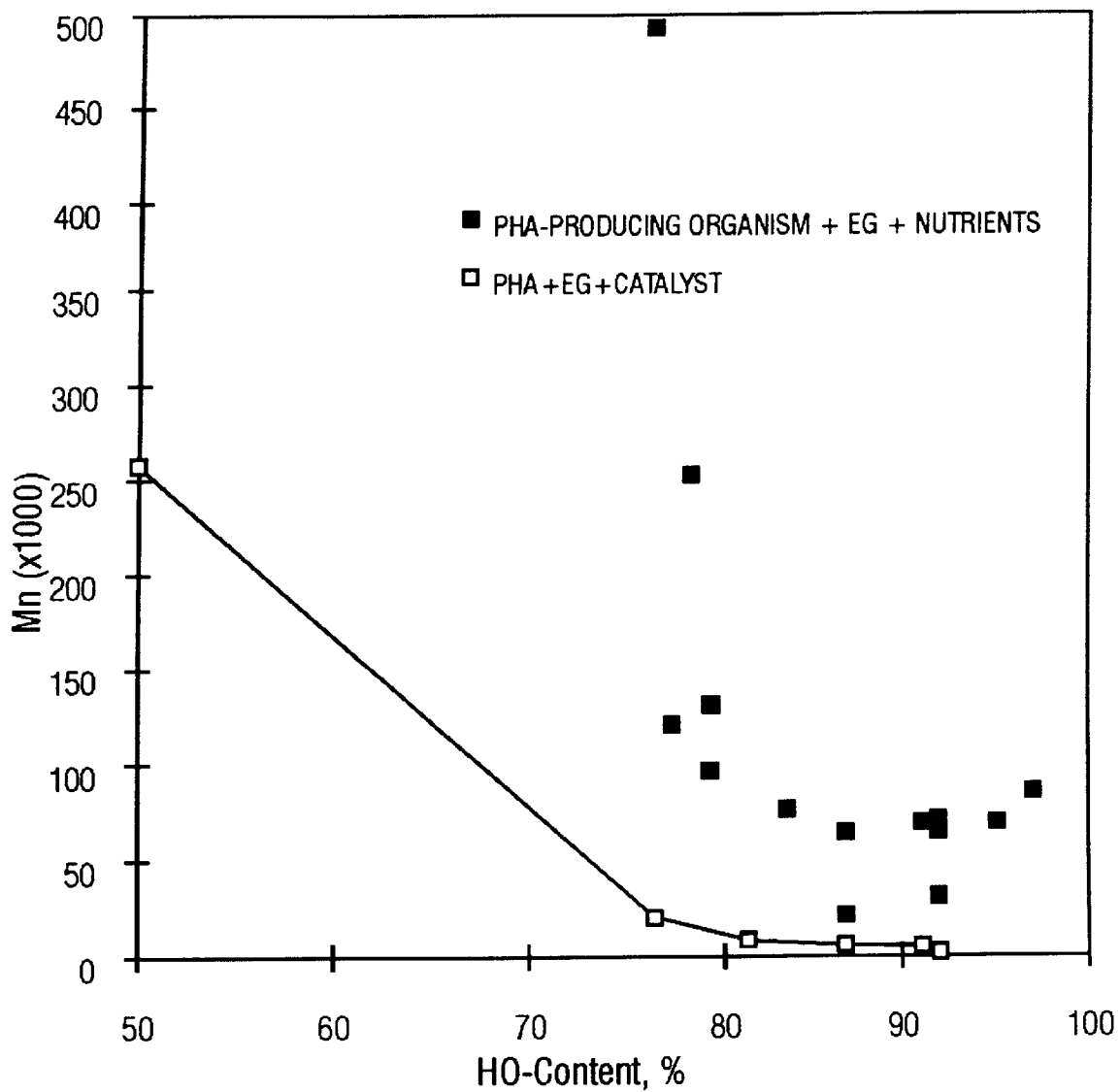
FIG. 1 demonstrates the advantages achieved by use of the methods of present invention for production of hydroxy-terminated PHA. The solid line shows the sharp decline in molecular weight of PHA when reacted with EG in the presence of a catalyst. The individually displayed data points, on the other hand, represent results obtained in accordance with the present invention, wherein hydroxy-terminated PHA is produced by cultivating a PHA-producing microorganism in the presence of an aliphatic diol or an aliphatic polyol. If a HO-content in the end-groups greater than 80% is desired, the MW of the PHA-diol is typically less than 7000 when produced by catalytic conversion. In accordance with the present invention, in contrast, the MW of the hydroxy-terminated PHA ranges, in these examples, from about 20,000 to greater than 80,000 depending on the strain of bacteria used. If HO-content in the end groups of greater than 90% is desired, the MW of the PHA-diol from the catalytic conversion is typically less than 3500 (2500 at 92% HO-content). In contrast, the present invention can PHA compositions having greater than 90% HO-content in a MW range up to greater than 80,000. The MW's can be influenced by the bacterial strain utilized in the method. If a high MW is desired (e.g. greater than about 60,000), *Alcaligenes eutrophus* may be preferably used. If lower MW's are desired (e.g. ~20,000), *Comamonas testosteroni* may be preferred. If intermediate molecular weights are desired, *Alcaligenes latus* may be preferred.

The embodiments of the present invention relate broadly to novel approaches for the production of PHA-derived materials having wide-ranging properties that can serve to increase the versatility of PHA for numerous applications without sacrificing biodegradability.

PHA is a polymer made from repeating units having the following general structure:

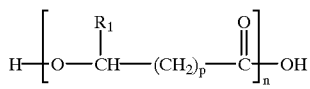

wherein $R_1$ is preferably an H, alkyl, or alkenyl; p is 0, 1, 2, or 3; and n is an integer. PHA can consist entirely of a single monomeric repeating unit, in which case it is referred to as a homopolymer. For example, polyhydroxybutyrate (PHB) homopolymer has repeating monomeric units wherein R1=C1 alkyl, and p=1. Copolymers, in contrast, contain two different types of monomeric units. PHBV, for example, is a copolymer containing polyhydroxybutyrate and polyhydroxyvalerate (R1=C2 alkyl, and p=1) units. Another copolymer of interest contains 3-hydroxybutyrate and 4-hydroxybutyrate units (3HB4HB). When three different types of repeating units are present the polymer is referred to as a terpolymer.

There is much interest in developing methods for the production of graft, random and block polymers and copolymers which contain PHA polymers in addition to other aliphatic moieties. In this way, it should be possible to generate polymers and copolymers with the necessary characteristics for a given application by altering the amounts and compositions of the PHA and of the other aliphatic moieties present. For the preparation of graft, block and random polymers and copolymers, it is often desirable to have available crystallizable polymers that have similar functional end-groups, and to have end-groups which are compatible with the end-groups of other macromers and monomers containing appropriate functionality. A method for the rapid and large scale production of end-functionalized PHA, therefore, would be useful in the preparation of new classes of graft, random and block copolymers with superior characteristics.

In a first embodiment of the present invention, there is provided a method of making hydroxy-terminated PHA in a PHA-producing microorganism by cultivating the microorganism in the presence of an aliphatic diol or an aliphatic polyol. Many of the aliphatic diols suitable for use in the present invention are represented by structures (1) and (2) below:

(1)

where n=0–25;

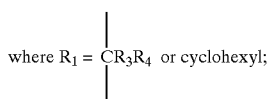

where $R_1 = CR_3R_4$ or cyclohexyl;

$R_2$=H or $CH_3(CH_2)_m$—, where m=0–25;
$R_3$ and $R_4$=H or $CH_3(CH_2)_p$— where p=0–25.

(2)

where n=1–10.

Examples of preferred aliphatic diols include ethylene glycol (EG), propylene glycol (PG), 1,3-propanediol (1,3-PD), neopentyl glycol (NG), 1,4-butanediol (1,4-BD), 1,4-cyclohexyldimethanol (1,4CHDM), 1,6-hexanediol (1,6-HD), diethylene glycol (DEG), and tetraethylene glycol (TEG) for linear hydroxy-terminated PHA's.

Many of the aliphatic polyols for use in the present invention are represented by structure (3) below:

(3)

where n=1–12;

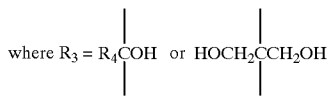

$R_4$=H or $CH_3(CH_2)_m$— where m=0–25.

Examples of preferred aliphatic polyols include glycerol (GL), pentaerythritol (PAE), sorbitol (SL), and mannitol (ML) for branched or star-shaped hydroxy-terminated PHA's. Also dianhydro derivatives of the aliphatic polyols, such as 1,4:3,6-dianhydrosorbitol or 1,4:3,6-dianhydroglucitol, could be used.

It has unexpectedly been found that PHA hydroxyl content can be increased by cultivating a PHA-producing microorganism in the presence of an aliphatic diol or polyol. Surprisingly, these compounds show little toxicity at concentrations in the culture medium (typically less than 5%) sufficient to generate PHA compositions having increased hydroxyl content (i.e. greater than 50%). Particularly preferred are those PHA compositions having a having a hydroxyl content greater than about 80 mol %, more preferably greater than 90%. However, PHA compositions having between 50 and 80 mol % hydroxyl end groups are also expected to be suitable for certain applications.

The PHA compositions so produced have molecular weights that can range up to greater than 100,000 while still having a high % HO-content. Furthermore, it is possible to vary the molecular weight of the hydroxy-terminated PHA by careful selection of the bacterial strain utilized. For example, if a high MW is desired (e.g. greater than about 60,000), *Alcaligenes eutrophus* may be preferably used. If lower MW's are desired (e.g. ~20,000), *Comamonas testosteroni* is preferred. If intermediate molecular weights are desired, *Alcaligenes latus* may be preferred. The selection of the aliphatic diol or polyol used in accordance with the present invention may also influence the MW of the hydroxy-terminated PHA obtained. Routine optimization of such experimental parameters can be readily determined by the skilled individual in this art.

It well know in the art that PHA polymer is produced by diverse types of microorganisms. (see for example, Alistair et al., Micro. Rev. 54(4), 450–472 (1990)) For example, strains from bacterial genus Alcaligenes (e.g. *eutrophus, latus*), Bacillus (e.g. *subtilis, megaterium*), Pseudomonas (e.g. *oleovorans, putida, fluorescent*), Aeromonas (e.g. *caviae, hydrophila*), *Azotobacter vinelandii, Comamonas testosteroni*, and others, produce PHA. Several bacterial strains are demonstrated herein to be useful in the production of hydroxyterminated PHA, including *Alcaligenes eutrophus, Alcaligenes latus*, and *Comamonas testosteroni*. Based on the demonstrated applicability of the disclosed method to three distinct strains, it is anticipated that the methods provided herein can be applied to essentially any microorganism which naturally produces PHA, or which has been genetically manipulated in a manner so as to effect PHA production.

Upon culturing a PHA-producing microorganism in the presence of aliphatic diols or aliphatic polyols, the PHA chains apparently are modified by a transesterification reaction. Although the exact mechanism of incorporation is not known, it may involve the addition of the aliphatic diol or polyol to the growing PHA chain by replacing the Coenzyme A at the end of a growing chain, serving as a chain-growth terminating agent. Such a mechanism might be used to explain the truncation of MW as compared to PHA biosynthesis in the absence of EG, etc. Also, it is clear that higher MW's are produced than in the case of random attack by EG catalyzed by Sn catalysts. The end-groups obtained are either primary hydroxyl groups arising from transesterified ethylene glycol units, or secondary hydroxyl groups from normal end units of the PHA chain.

The PHA compositions produced according to the first embodiment of the present invention can be recovered from the PHA-producing microorganism by conventional methods. Typically, a solvent-based approach is utilized, wherein the cells are harvested, dried, and the PHA is extracted with a solvent capable of dissolving PHA from other bacterial components. However, methods suitable for the recovery of PHAs from microbial and other biomass sources are expected to also be suitable for the recovery of hydroxy-terminated PHA made in accordance with the present invention.

In a second embodiment of the present invention, there are provided hydroxy-terminated PHA compositions. The compositions are preferably produced by the method disclosed in the first embodiment of the present invention, wherein a PHA-producing microorganism is grown in the presence of an aliphatic diol or polyol. The structure of the hydroxy-terminated PHA can vary depending on cultivating conditions, for example the carbon source utilized, and which aliphatic diol or aliphatic polyol is used in the culture medium. The MW's of the hydroxy-terminated PHA compositions are greater than 3,000, and can range up to 100,000 or more. Thus, in accordance with the method of the present invention, it is possible to produce hydroxy-terminated PHA's having molecular weights much higher than was previously possible. In addition, the HO-content of the PHA compositions obtainable from the microorganisms is typically greater than 70%, preferably greater than 80%, and more preferably greater than 90%.

In one important embodiment, the PHA compositions comprise hydroxy-terminated PHA, wherein the compositions have an end group hydroxyl content greater than 90 mol % and a molecular weight greater than 3000. Further provided are PHA compositions wherein the molecular weight is greater than about 20,000 and the end group hydroxyl content is greater than 80%, or those where the molecular weight is greater than about 100,000 and the end group hydroxyl content is greater than about 70%. Although hydroxyl contents greater than 70 or 80% may be preferred for many applications, other applications may not necessarily require such levels. PHA compositions produced in accordance with the present invention which have greater than 50% hydroxyl content, therefore, are also expected to be useful in a variety of applications.

These high MW PHA compositions are desirable for use in the production of polymer and copolymer compositions since many of the beneficial properties of high MW PHA's, such as hydrophobicity, biodegradability in soil and aqueous environments and biodegradability in humans and animals, are retained in a polymer or copolymer which contains the PHA.

Hydroxy-terminated PHAs produced in accordance with this invention are useful in the production of biodegradable graft, block and random polymers and copolymers comprising hydroxy-terminated PHAs and other suitable polymers, oligomers or monomers. Therefore, several embodiments of the present invention relate to methods of using the hydroxy-terminated PHA of the present invention in the production of graft, block or random polymer and copolymer compositions, and the PHA-containing polymer and copolymer compositions produced therefrom. The molecular weight of the hydroxy-terminated PHA, by appropriate selection of the bacterial strain and aliphatic diol or polyol used, can be manipulated such that the properties required or desired for a given PHA-containing polymer or copolymer may be more readily achieved.

In a particularly important embodiment of the present invention, there is provided a method of using the hydroxy-terminated PHA of the present invention to produce a polymer or copolymer, wherein the PHA is reacted with a coupling agent. The polymer or copolymer so produced could be, for example, a block polymer or copolymer. Also provided are the polymer and copolymer compositions produced therefrom. Suitable coupling agents may include, for example, alkyl or aryl diisocyanate or triisocyanate, phosgene, alkyl or diaryl carbonate, a monomeric organic diacid, a monomeric organic diacid chloride, a monomeric organic diacid anhydride or a monomeric organic tetraacid dianhydride. Alternatively, the coupling agent can be an oligomer with end-groups that are reactive with hydroxy-terminated PHA, such as carboxy-terminated oligomeric polyesters or a isocyanate-terminated oligomeric polyol or polyester. This approach can be used, for example, to produce polyesters, copolyesters, polyester-carbonates, and polyester urethanes.

In a further embodiment of the present invention, there is provided a method of using the hydroxy-terminated PHA of the present invention to produce a polymer of copolymer, wherein the PHA is reacted with a coupling agent and with a different hydroxy-terminated moiety. The polymer so produced could be, for exanple, a block or random block polymer or copolymer. Also provided are the polymer and copolymer compositions produced therefrom. Suitable coupling agents may include, for example, alkyl or aryl diisocyanate or triisocyanate, phosgene, alkyl or diaryl carbonate, a monomeric organic diacid, a monomeric organic diacid chloride, a monomeric organic diacid anhydride or a monomeric organic tetraacid dianhydride. Alternatively, the coupling agent can be an oligomer with end-groups that are reactive with hydroxy-terminated PHA, such as a carboxy-terminated oligomeric polyester or polyamide, or a isocyanate-terminated oligomeric polyol, polyester or polyamide. The hydroxy-terminated moieties for use in this embodiment can include polyester diols such as polycaprolactone diol, polybutylene succinate diol, polybutylene succinate co-butylene adipate diol, polyethylene succinate diol, and similar aliphatic polymeric and copolymeric diols. Alternatively, the hydroxy-terminated moiety can be a polyether diol such as a polyethylene oxide-diol, polypropylene oxide-diol, or polyethylene oxide-propylene oxide diol. This approach can be used, for example, to produce polyesters, copolyesters, polyester carbonates, polyester urethanes, polyester ethers, polyester amides, copolyester ethers, polyester ether carbonates, and polyester ether urethanes.

In yet a further embodiment of the present invention, there is provided a method of using the hydroxy-terminated PHA of the present invention to produce a random or random block polymer or copolymer, wherein the PHA is reacted with a different polyester, copolyester, polyamide, or organic dicarboxylic acid in the presence of a catalyst. Also provided are the PHA-containing polymer or copolymer compositions produced therefrom. Suitable polyesters and copolyesters can include polyethylene terephthalate, polybutylene terephthalate, polycaprolactone, polyhydroxyalkanoates, polylactides, polyglycolides, polyethylene succinate, polybutylene succinate, polyethylene adipate, polyethylene succinate adipate, and other combinations of such polyesters or copolyesters. Suitable dicarboxylic acids may include, for example, oxalic acid, malonic acid, succinic acid, glutaric acid, adipic acid, azealic acid, terephthalic acid, phthalic acid, maleic acid, fumaric acid, and their anhydrides. Suitable polyamides may include for example nylon 6, nylon 66, and nylon 12. The catalyst can be, for example, Sn, Sb, or Ti catalysts. This approach can be used to produce polyesters, copolyesters, and polyester amides.

In yet a further embodiment of the present invention, there is provided a method of using the hydroxy-terminated PHA of the present invention to produce a block polymer or copolymer, comprising the steps of reacting the PHA with a reactive monomer. Also provided are the PHA-containing copolymer compositions produced therefrom. Where needed, catalysts and other reactants known in the art to facilitate the reaction, are used. The reactive monomer used in this embodiment can include, for example, alkyl epoxides such as ethylene oxide and propylene oxide, lactones such as caprolactone, butyrolactone, propiolactone, valerolactone, lactams such as caprolactam, and formaldehyde. This approach can be used to produce polyesters, copolyesters, polyester ethers, polyester amides, and polyester acetals.

In yet a further embodiment of the present invention, there is provided a method of using the hydroxy-terminated PHA of the present invention to produce thermoset resins, wherein the hydroxy-terminated PHA is first derivatized with a derivatizing agent, followed by curing the derivatized PHA with a curing agent. Also provided are the thermoset resin compositions produced therefrom. The curing agents suitable for use in this embodiment can include amide, amine, dicarboxylic acid or dicarboxylic acid anhydride based agents, in addition to other such agents well known in the art. Similarly, the derivatizing agent can be selected from those known in the art. One preferred derivatizing agent for use in this embodiment is epichlorohydrin, where the resulting derivatized PHA is a mono- or di-glycidyl PHA.

Suitable approaches for the production of the novel PHA-containing polymer and copolymer compositions described in the above embodiments are further illustrated below. A block copolymer of the present invention, for example, can comprise hydroxy-terminated PHA and hydroxy-terminated aliphatic polyesters and polyethers such as those selected from hydroxy-terminated polyoxyethylenes, polycaprolactone diol, polybutylene succinate diol, polyethylene succinate diol, and polybutylene succinate co-butylene adipate diol. The polymers and copolymers that can be made include, for example, copolyesters, polyester carbonates, polyester ethers, polyester urethanes, polyester amides, polyester acetals, and others.

Block copolyesters may be synthesized by the reaction of a hydroxy-terminated PHA with an organic diacid, an organic diacid chloride, an organic acid anhydride, an organic acid dianhydride, a tetracarboxylic acid dianhydride, etc. The example below illustrates the reaction of the PHA-diol with an organic diacid chloride.

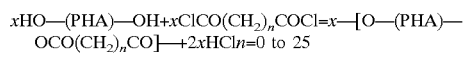

Block copolyesters may also be made by reaction of the PHA-diol with lactones such as beta-butyrolactone, delta-valerolactone, beta-propiolactone, epsilon-caprolactone, etc. They can also be made by reaction of the PHA-diol with lactides and glycolides including L-lactide, L-glycolide, D,L-dilactide, etc. The lactones, lactides, and glycolides selected may be optically active or inactive, depending upon the application. Catalysts for the reactions are known in the art and can include compounds of Sn [e.g. Sn octanoate (see for example U.S. Pat. No. 5,321,088)], Ti [e.g. Ti(OBu)$_4$ (see for example JP 05 202173)], Zn [e.g. Et$_3$Zn, (see for example JP 05 132549)], and Al [e.g. Me$_3$Al or Et$_3$Al (see for example CA 111:120806)].

Block polyester-carbonates may be synthesized by the reaction of hydroxy-terminated PHA with phosgene or alkyl or aryl carbonate, [e.g. diphenyl carbonate (see for example EP 684,270)]. The example below illustrates the reaction of the PHA-diol with phosgene.

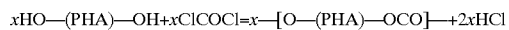

Block polyester ethers can be made by reaction of the PHA-diol with an alkylene oxide such as ethylene oxide (EO) or propylene oxide (PO) or their mixtures [see for example EP 570,121]. The reaction with EO as illustrated below.

$x$HO—(PHA)—OH+$z$EO=H—[(EO)$y$—(PHA)$x$—O(EO)$z$—]H

Block polyester-urethanes may be synthesized by the reaction of hydroxy-terminated PHA with isocyanates, diisocyanates such as hexamethylene diisocyanate (HMDI), dicyclohexyl methane 4,4'-diisocyanate (CHMDI), isophorone diisocyanate (IPDI) and triisocyanates. The example below illustrates the reaction of the PHA-diol with HMDI.

$x$.HO—(PHA)—OH+$x$OCN(CH$_2$)$_6$NCO=$x$—[O—(PHA)—OCON(CH$_2$)$_6$NOC]—

Block polyester-amides may be synthesized by the catalyzed reaction of hydroxy-terminated PHA with lactams (see for example JP 04 283233), or by reaction of the diol with an organo diacid chloride and hexamethylene diamine (see for example, CA 118:81550). The example below illustrates the reaction of PHA-diol with beta-caprolactam (b-CL).

$x$HO—(PHA)—OH+$nb$-CL=—[O—(PHA)—O]$x$—[CO(CH$_2$)$_5$NH]$n$—

Polyester acetals can be made by reaction of the PHA-diol with formaldehyde followed by endcapping with acetic anhydride. Catalysts for the reaction include Sn compounds such as (Bu)$_2$Sn(OCH$_3$)$_2$ (see for example JP 06 65468) and quaternary ammonium compounds such as Bu$_4$N+Oac- (see for example JP 05 43638).

$x$HO—(PHA)—OH+2$xy$CH$_2$O+Ac2O=$x$Ac(OCH$_2$)$n$O—(PHA)—O(CH2O)$m$Ac

Use of the hydroxy-terminated PHA compositions of the present invention for production of novel random polymers and copolymers is illustrated below. Random polymers made in this way can include copolyesters, polyester carbonates, polyester ethers, polyester urethanes, an polyester amides Random copolyesters may be synthesized by the reaction of the PHA-diol with PET in the presence of a Sn catalyst in DMSO solvent at greater than about 100° C.

$x$HO—(PHA)—OH+$y$—(EG)—(TPA)=—(HA)$x$—(EG)$y$—(TPA)$y$—

Random block copolyester amides could also be synthesized by reaction of the PHA-diol with a nylon (e.g. nylon 12) in the presence of a catalyst [e.g. Zn(OAc)$_2$, (see for example CA 118:40168)] or by reaction of PHA-diol, a diacid such as dodecanedioic acid (DDDA) and caprolactam (CL) in the presence of a catalyst such as Sb$_2$O$_3$ (see for example JP 04 283233) as shown in the example below.

$x$HO—(PHA)—OH+$y$DDDA+$z$CL=—[CL]$z$[O—(PHA)—O]$x$[DDDA]$y$—

Random block polyester-ethers may be synthesized by the reaction of the PHA-diol, a polyalkylene glycol and a diacid, diacid chloride, or a dianhydride. The example below illustrates the reaction of PHA-diol, polyethylene glycol and a diacid chloride.

$x$HO—(PHA)—OH+$y$ClCORCOCl+$z$H—(OCH$_2$CH$_2$)$n$—OH=—[O—(PHA)$x$—O(CORCO)$y$O(CH$_2$CH$_2$O)$nz$]—+2$y$HCl

The hydroxy-terminated PHA produced in accordance with the present invention can also be converted into biodegradable thermoset resins by selected, known reactions. For example, conversion of the diol with epichlorohydrin to PHA-diepoxide followed by a curing step can give a biodegradable epoxy resin, depending on selection of the curing agent and other components of the formulation.

$x$HO—(PHA)—OH+2$x$Clepox=$x$[epox—O—(PHA)—O—epox]$x$
[epox—O—(PHA)—O—epox]+curing agent=cured resin Other thermoset resins that can be made using PHA-diol as a starting material include polyurethanes and unsaturated polyesters.

The following examples are included to demonstrate preferred embodiments of the invention. It should be appreciated by those of skill in the art that the techniques disclosed in the examples which follow represent compositions and methods discovered by the inventor to function effectively in the practice of the present invention, and thus can be considered to constitute examples of preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Synthesis of Diol-terminated Poly(3-hydroxybutyrate) by Transesterification with Ethylene Glycol 100 g poly(3-hydroxybutyrate) was dissolved in 300 ml diglyme at 140° C. in a 4-necked flask equipped with a thermometer, overhead stirrer and reflux condenser, under nitrogen. To this 25 ml ethylene glycol was added and the mixture allowed to stir for about 5 minutes. Following this, 0.14 mL dibutyltin dilaurate was added via a syringe, and the reaction mixture was stirred for 7 hours. During the reaction, 0.14 mL dibutyltin dilaurate was added every 1.25 h (0 h, 1.25 h, 2.5 h, 3.75 h, 5 h, 6.25 h). At the end of 7.5 h, the solution was immediately filtered hot, and the product precipitated by pouring it into approximately 10 times excess volume of cold distilled water. The product was separated by filtration under vacuum, washed with distilled water three times, and dried under vacuum at 80° C. for 24 h. An NMR method was adapted from the literature (Spyros, A., et. al.; Macromolecules (1997), 30, 327–9) to determine the end groups of PHA's. Since phosphorus in both hydroxyl and carboxyl end groups are present in the same P-31 spectrum, a ratio can be calculated by simple integration of the peaks. Molecular weight was determined by GPC using polystyrene (PS) calibration.

| Preparation of PHA-diol by reaction of PHB with EG. | | |
|---|---|---|
| Time, hours | Mn | HO-content % of endgroups |
| 0 | 260 k | 50 |
| 1.25 | 18 k | 77 |
| 2.5 | 5.0 k | 82 |
| 3.75 | 3.0 k | 87 |
| 6.25 | 2.0 k | 91 |
| 7.5 | 1.6 k | 92 |

EXAMPLE 2

*Alcaligenes eutrophus* strain TRON721 was grown in 250-ml shake flasks containing 50 ml of a minimal salt medium plus glucose (2%), Na-4-hydroxybutyrate (0.5%) and ethylene glycol (EG). Cells were grown at 30° C. for 4 days. The MW of the PHA was measured by GPC using a PS standard. Content of hydroxyl end groups was determined by the NMR technique referenced in Comparative Example 1.

| EG (%) | CDW (mg/ml) | PHA Content (%) | Mw (×1000) | Mn (×1000) | mol % OH |
|---|---|---|---|---|---|
| 0 | 351 | 70.9 | 884 | 331 | 43 |
| 1 | 354 | 72.6 | 201 | 75 | 84 |
| 3 | 327 | 70.9 | 143 | 68 | 91 |
| 5 | 175 | 49.1 | 185 | 84 | 97 |

At concentrations greater than about 3%, EG has a toxic effect on the bacteria as shown by a significant drop in CDW and PHA content.

EXAMPLE 3

*Alcaligenes eutrophus* strain TRON721 was grown in the same conditions as in Example 1, except the medium contained glucose (2%), Na-4-hydroxybutyrate (0.5%), Na-butyrate (0.1%) and ethylene glycol (2%). Cell dry weight (CDW) was 500 mg/flask and PHA content was 77.2%. This PHA contained 15.2% 4-hydroxybutyric acid and 84.8% 3-hydroxybutyric acid. The MW (Mn) as determined by GPC using a PS standard was 66,700 and the mole-% hydroxyl end groups was 94.6 by NMR analysis.

EXAMPLE 4

*Alcaligenes eutrophus* strain TRON721 was grown in 2-L shake flasks containing 1-L of a minimal salt medium with glucose (2%), Na-butyrate (0.1%) and ethylene glycol (2%). Cells were grown at 34° C. for 3 days. The PHB production was 1.49 g/L with molecular weight by GPC using a PS standard Mw=298,000 and Mn=64,000. The mole-% hydroxyl end groups was 92.43% by NMR analysis.

EXAMPLE 5

*Alcaligenes eutrophus* strain TRON 721 was grown in 250-ml shake flasks containing 50 ml Luria-Bertani (LB) medium plus 2% oleic acid and different concentrations of ethylene glycol (EG). The culture flasks were incubated at 30° C. for 3 days in a shaker (New Brunswick) orbiting at 250 rpm. Cells were harvested, dried, and extracted with chloroform at 100° C. for 2 hours. The MW of the PHB was measured by GPC using a polystyrene standard.

| EG (%) | CDW (mg/ml) | PHB Content (%) | Mw (×1000) | Mn (×1000) |
|---|---|---|---|---|
| 0 | 12.6 | 70 | 3470 | 675 |
| 1 | 12.8 | 63.5 | 794 | 319 |
| 2 | 11.4 | 55 | 308 | 217 |
| 3 | 11.7 | 64 | 180 | 60 |

EXAMPLE 6

*Alcaligenes latus* (ATCC 29713) was grown in 250 ml shake flasks containing 50 ml LB medium plus 2% sucrose and 3% ethylene glycol (EG). The culture flasks were incubated at 30° C. for 3 days in a shaker (New Brunswick) orbiting at 250 rpm. Cells were harvested, dried, and extracted with chloroform at 100° C. for 2 hours. The MW of the PHB was measured by GPC using a polystyrene standard.

| EG (%) | CDW (mg/ml) | PHB Content (%) | Mw (×1000) | Mn (×1000) |
|---|---|---|---|---|
| 0 | 9.7 | 67.6 | 698 | 341 |
| 3 | 5.5 | 47.6 | 69 | 31 |

The content of hydroxyl endgroups of the polymer made with 3% EG added was 91.5% by NMR analysis.

EXAMPLE 7

*Comamonas testosteroni* was grown in 250-ml shake flasks containing 50 ml LB medium plus 2% oleic acid and different concentrations of ethylene glycol (EG). The culture flasks were incubated at 30° C. for 3 days in a shaker (New Brunswick) orbiting at 250 rpm. Cells were harvested, dried, and extracted with chloroform at 100° C. for 2 hours. The MW of the PHB was measured by GPC using a polystyrene standard.

| EG (%) | CDW (mg/ml) | PHB Content (%) | Mw (× 1000) | Mn (× 1000) |
|---|---|---|---|---|
| 0 | 3.3 | 23.5 | 247 | 96 |
| 1 | 5.7 | 33.6 | 59 | 37 |
| 2 | 4.3 | 29.5 | 34 | 19 |
| 3 | 4.3 | 32.4 | 40 | 22 |

EXAMPLE 8

*Comamonas testosteroni* was grown in a 10-L fermenter (Braun Biostat B) containing 8.5 L of medium containing (g/L):

| K2HPO4 | 4.7 |
|---|---|
| KH2PO4 | 1.1 |
| MgSO4—7H2O | 5 |
| NaCl | 5 |
| Yeast extract | 15 |
| ferric citrate | 0.01 |
| EDTA | 0.04 |
| oleic acid | 50 ml |
| ethylene glycol | 30 ml | pH was adjusted to 6.5 with ammonia (28%). Agitation was 600–1200 rpm with dissolved oxygen minimum of 20%. Aeration was 5 L/minute. The culture was harvested after 65 hours and cells were extracted with chloroform at room temperature for 24 hours.

| CDW (g/L) | PHB Content (%) | Mw (×1000) | Mn (×1000) |
|---|---|---|---|
| 16.4 | 22 | 58.6 | 21.1 |

The hydroxyl endgroup content was found to be 87% by NMR analysis.

EXAMPLE 9

*Alcaligenes eutrophus* strain TRON721 and Alcaligenes latus ATCC 29713 were grown in 250-ml shake flasks containing 50 ml LB medium plus 2% glucose (A.eutrophus) or 2% sucrose (A.latus) and with or without 1% neopentyl glycol (NG). The culture flasks were incubated at 30° C. for 3 days in a shaker (New Brunswick) orbiting at 250 rpm. Cells were harvested, dried, and extracted with chloroform at 100° C. for 2 hours. The molecular weight of the PHB was measured by GPC using a polystyrene standard.

|  | NG (%) | CDW (mg/ml) | PHB Content (%) | Mw (×1000) | Mn (×1000) |
|---|---|---|---|---|---|
| A. Eutrophus | 0 | 9.3 | 36 | 3759 | 661 |
|  | 1 | 9.5 | 29 | 3559 | 550 |
| A. Latus | 0 | 7.8 | 58 | 614 | 249 |
|  | 1 | 3.2 | 24 | 396 | 182 |

EXAMPLE 10

The experiments described in example 9 were repeated except that diethylene glycol was used.

|  | DEG (%) | CDW (mg/ml) | PHB Content (%) | Mw (×1000) | Mn (×1000) |
|---|---|---|---|---|---|
| A. Eutrophus | 0 | 9.3 | 36 | 3759 | 661 |
|  | 1 | 9.1 | 45 | 735 | 243 |
| A. Latus | 0 | 7.8 | 58 | 614 | 249 |
|  | 1 | 6.4 | 61 | 65 | 36 |

EXAMPLE 11

The experiments described in example 9 were repeated except that tetraethylene glycol was used.

|  | TEG (%) | CDW (mg/ml) | PHB Content (%) | Mw (×1000) | Mn (×1000) |
|---|---|---|---|---|---|
| A. Eutrophus | 0 | 9.3 | 36 | 3759 | 661 |
|  | 1 | 9.1 | 57 | 849 | 274 |
| A Latus | 0 | 7.8 | 58 | 614 | 249 |
|  | 1 | 7.9 | 52 | 128 | 84 |

EXAMPLE 12

*Alcaligenes eutrophus* strain TRON 721 was grown in 250-ml shake flasks containing 50 ml LB medium plus 2% glucose and different concentrations of propylene glycol (PG). The culture flasks were incubated at 30° C. for 4 days in a shaker (New Brunswick) orbiting at 250 rpm. Cells were harvested, dried, and extracted with chloroform at 100° C. for 2 hours. The MW of the PHB was measured by GPC using a PS standard.

| PG (%) | CDW (mg/ml) | PHB Content (%) | Mw (×1000) | Mn (×1000) | % OH |
|---|---|---|---|---|---|
| 1 | 10.7 | 57 | 346 | 131 | 80 |
| 2 | 11.0 | 54 | 272 | 120 | 78 |
| 3 | 10.2 | 49 | 227 | 97 | 80 |
| 4 | 11.1 | 47 | 187 | 69 | 92 |
| 5 | 11.1 | 56 | 180 | 63 | 87 |

EXAMPLE 13

*Alcaligenes eutrophus* strain TRON 721 was grown in 250-ml shake flasks containing 50 ml LB medium plus 2% glucose and different concentrations of pentaerythritol (PAE). The culture flasks were incubated at 30° C. for 4 days in a shaker (New Brunswick) orbiting at 250 rpm. Cells were harvested, dried, and extracted with chloroform at 100° C. for 2 hours. The MW of the PHB was measured by GPC using a PS standard.

| PAE (%) | CDW (mg/ml) | PHB Content (%) | Mw (×1000) | Mn (×1000) | % OH |
|---|---|---|---|---|---|
| 0 | 8.7 | 57 | 1,362 | 420 | 51 |
| 0.25 | 10.4 | 46 | 778 | 254 | 79 |
| 0.5 | 9.3 | 52 | 1,269 | 493 | 77 |
| 1.0 | 8.4 | 51 | 1,308 | 406 | (Not Determined) |
| 2.0 | 9.1 | 51 | 1,535 | 728 | 67 |

EXAMPLE 14

Synthesis of 50:50 Poly(3-hydroxybutyrate)-block-Poly(ε-caprolactone) Copolyesterurethane 4.5 g P3HB diol obtained as described in Example 8 (87% of end-groups determined to be hydroxyl, 13% carboxyl, Mn=19,300 by end-group analysis, Mn=21,100 by GPC relative to PS, 0.23 mmol) and 4.5 g polycaprolactone (PCL) diol (Aldrich, Mn=2000 reported by vendor, 2.2 mmol) were dissolved in 200 ml 1,2-dichloroethane in a 500 ml round-bottom flask. The solution was refluxed for about 20 hours via a soxhlet extractor with a thimble containing ~15 g activated 4 Å molecular sieves, to remove any residual water from the diols as a water/dichloroethane azeotrope. Following this, most of the dichloroethane was distilled off until a still stirrable, viscous solution remained. A nitrogen purge was maintained at all times. The distillation head was then removed and the flask fitted with an overhead stirrer and reflux condensor. A solution of 0.44 g hexamethylene diisocyanate (2.6 mmol) in 5 ml anhydrous 1,2-dichloroethane (EM Science, kept over molecular sieves for at least 24 h prior to use) was prepared, which was then slowly added via an addition funnel in two parts. Approximately half was added at the beginning of the reaction over a 2 h period, and the other half was added 12 h later, also over a 2 h period. A solution of 42 $\mu$l of the catalyst, dibutyltin dilaurate, was prepared in 5 mL anhydrous 1,2-dichloroethane. 1.5 ml of this solution was added via a syringe at the beginning of the reaction. The reaction mixture was stirred at 79° C. for about 110 hours. The product was recovered by precipitation in 1 L methanol, and further purified by redissolving in chloroform, reprecipitating in 1 L petroleum ether and drying in a vacuum oven at approximately 80° C. for about 12 hours. Yield: 8.4 g. Molecular weight determination by GPC with PS calibration showed the product to have Mw=102,000 and Mn=52,000. Characterization by DSC of this polymer showed two endothermic peaks at 38° C. and 161° C. upon heating, and two exothermic peaks at 91° C. and 4° C. on cooling. The sample in tensile testing, showed 637% elongation at break and tensile strength of 1528 psi.

EXAMPLE 15

Synthesis of 75:25 Poly(3-hydroxybutyrate)-block-Poly(ε-caprolactone) Copolyesterurethane 4.5 g P3HB diol obtained as described in Example 8 (87% of end-groups determined to be hydroxyl, 13% carboxyl, Mn=19,300 by end-group analysis, Mn=21,100 by GPC relative to PS, 0.23 mmol) and 1.5 g PCL diol (Aldrich, Mn=2000 reported by vendor, 0.75 mmol) were dissolved in 200 ml 1,2-dichloroethane in a 500 ml round-bottom flask. The solution was refluxed for about 18 h via a soxhlet extractor with a thimble containing ~15 g activated 4 Å molecular sieves, to remove any residual water from the diols as a water/dichloroethane azeotrope. Following this, most of the dichloroethane was distilled off until a still stirrable, viscous solution remained. A nitrogen purge was maintained at all times. The distillation head was then removed and the flask fitted with an overhead stirrer and reflux condensor. A solution of 0.17 g hexamethylene diisocyanate (1.03 mmol) in 5 ml anhydrous 1,2-dichloroethane (EM Science, kept over molecular sieves for at least 24 h prior to use) was prepared, which was then slowly added to the flask via an addition funnel. A solution of 28 $\mu$l of the catalyst, dibutyltin dilaurate, was prepared in 5 mL anhydrous 1,2-dichloroethane. 1.5 ml of this solution was added via a syringe at the beginning of the reaction. The reaction mixture was stirred at 79° C. for 141 hours. The product was then recovered by precipitation in 1 L methanol, and further purified by redissolving in chloroform, reprecipitating in 1 L petroleum ether and drying in a vacuum oven at 80° C. for 12 hours. Yield: 5.6 g. Molecular weight determination by GPC with PS calibration showed the product to have Mw=59,900 and Mn=26,850.

EXAMPLE 16

A copolyester urethane was prepared with 25 g P3HB diol, 25 g PCL-diol and 4.4 g HMDI by essentially following the procedure of Example 14, with the exception that the P3HB-diol of Mn=2000 and 92% HO-endgroup content, was made by chemical transesterification of PHB and EG in the presence of a stannate catalyst, and the reaction time was approximately 24 hours. Yield: 42.3 g. Molecular weight determinations were made by GPC with PS calibration and showed the product to have Mw=74,950 and Mn=44,100. The final product in tensile testing, showed 101% elongation at break and tensile strength of 1105 psi.

All of the methods and compositions disclosed and claimed herein can be made and executed without undue experimentation in light of the present disclosure. While the compositions and methods of this invention have been described in terms of preferred embodiments, it will be apparent to those of skill in the art that variations may be applied to the compositions and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A hydroxy-terminated PHA composition having a number average molecular weight greater than about 3000, and wherein the end group hydroxyl content is greater than 90 mol %.

2. A PHA composition comprising hydroxy-terminated PHA, wherein said PHA has a number average molecular weight of greater than about 3000, wherein the end group hydroxyl content is greater than 90 mol %.

3. A PHA composition comprising hydroxy-terminated PHA, wherein the end group hydroxyl content is greater than 55 mol % and the number average molecular weight of said hydroxy-terminated PHA is greater than about 20,000.

4. The PHA composition of claim 3, wherein the end group hydroxyl content is greater than 80 mol % and the number average molecular weight of said hydroxy-terminated PHA is greater than about 20,000.

5. The PHA composition of claim 3, wherein the end group hydroxyl content is greater than 70 mol % and the number average molecular weight of said hydroxy-terminated PHA is greater than about 100,000.

6. The PHA composition of claim 3, wherein the end group hydroxyl content is greater than 55 mol % and the number average molecular weight of said hydroxy-terminated PHA is greater than about 250,000.

* * * * *